(12) United States Patent
Park

(10) Patent No.: US 9,685,618 B2
(45) Date of Patent: Jun. 20, 2017

(54) BLUE LUMINESCENT COMPOUNDS

(71) Applicant: E I DU PONT DE NEMOURS AND COMPANY, Wilmington, DE (US)

(72) Inventor: Kyung-Ho Park, Wilmington, DE (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 285 days.

(21) Appl. No.: 14/391,720

(22) PCT Filed: Apr. 19, 2013

(86) PCT No.: PCT/US2013/037312
§ 371 (c)(1),
(2) Date: Oct. 10, 2014

(87) PCT Pub. No.: WO2013/163019
PCT Pub. Date: Oct. 31, 2013

(65) Prior Publication Data
US 2015/0076465 A1     Mar. 19, 2015

Related U.S. Application Data

(60) Provisional application No. 61/636,845, filed on Apr. 23, 2012.

(51) Int. Cl.
| | | |
|---|---|---|
| *H01L 51/00* | (2006.01) | |
| *C07F 15/00* | (2006.01) | |
| *C09K 11/06* | (2006.01) | |
| *H05B 33/14* | (2006.01) | |
| *H01L 51/50* | (2006.01) | |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1007* (2013.01); *C09K 2211/1044* (2013.01); *C09K 2211/185* (2013.01); *H01L 51/5016* (2013.01)

(58) Field of Classification Search
CPC . H05B 33/14; C07F 15/0033; H01L 51/0085; H01L 51/5016; C09K 11/06; C09K 2211/1007; C09K 2211/1044; C09K 2211/185
See application file for complete search history.

(56) References Cited

U.S. PATENT DOCUMENTS

| | | |
|---|---|---|
| 6,670,645 B2 | 12/2003 | Grushin et al. |
| 6,699,599 B2 | 3/2004 | Li et al. |
| 6,875,524 B2 | 4/2005 | Hatwar et al. |
| 7,745,017 B2 | 6/2010 | Nakamura |
| 7,816,016 B1 | 10/2010 | Herron |
| 2004/0102577 A1 | 5/2004 | Hsu et al. |
| 2004/0127637 A1 | 7/2004 | Hsu et al. |
| 2005/0158577 A1 | 7/2005 | Ishibashi et al. |
| 2005/0205860 A1 | 9/2005 | Hsu et al. |
| 2009/0200927 A1* | 8/2009 | D'Andrade ......... H01L 51/5036 313/504 |
| 2010/0140605 A1 | 6/2010 | Shibata et al. |

FOREIGN PATENT DOCUMENTS

| | | |
|---|---|---|
| WO | 03/008424 A1 | 1/2003 |
| WO | 03/040257 A1 | 5/2003 |
| WO | 03/063555 A1 | 7/2003 |
| WO | 2004/016710 A1 | 2/2004 |
| WO | 2009/018009 A1 | 2/2009 |

OTHER PUBLICATIONS

Takizawa et al, Phosphorescent Iridium Complexes Based on 2-Phenylimidazo[1,2-a]pyridine Ligands: Tuning of Emission Color toward the Blue Region and Application to Polymer Light-Emitting Devices, vol. 46, No. 10, pp. 4308-4319, Apr. 13, 2007.*
Alan Spivey, Chemistry II (Organic) Heteroaromatic Chemistry Lecture 8—Diazoles & Diazines: Properties, Syntheses & Reactivity, pp. 1-5, Imperial College London.*
CRC Handbook of Chemistry and Physics, 81$^{st}$ edition, (2000-2001 (Book Not Included).
Komo et al, Chem. Lett., 32, 252, (2003) (Not Included).
Gustafsson et al, Nature, "Flexble Light-Emitting Diodes Made From Soluble Conducting Polymers", vol. 357, pp. 477-479 (Jun. 11, 1992).
Kirk-Othmer Encyclopedia of Chemical Technology, 4$^{th}$ Edition, vol. 18, p. 837-860, 1996, Y. Wang.
PCT Search Report, Intl. Application No. PCT/US2013/037312 dated Jul. 24, 2013.

* cited by examiner

Primary Examiner — Alexander Kollias

(57) ABSTRACT

There is provided a compound having Formula I

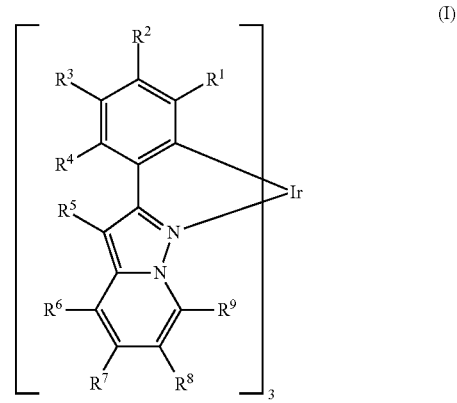

In the formula: $R^{1-4}$ are the same or different and are H, D, alkyl, silyl, aryl, deuterated alkyl, deuterated silyl, deuterated aryl, or an electron-withdrawing group; $R^5$ is H, D, alkyl, aryl, deuterated alkyl, or deuterated aryl; and $R^6$-$R^9$ are the same or different and are H, D, alkyl, silyl, aryl, deuterated alkyl, deuterated silyl, or deuterated aryl. At least one of $R^{1-4}$ is an electron-withdrawing group.

15 Claims, 2 Drawing Sheets

BLUE LUMINESCENT COMPOUNDS

RELATED APPLICATION DATA

This application claims priority under 35 U.S.C. §119(e) from U.S. Provisional Application No. 61/636,845, filed on Apr. 23, 2012, which is incorporated by reference herein in its entirety.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I

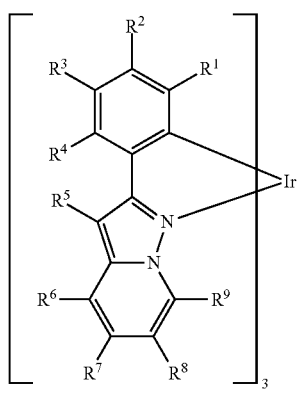

(I)

wherein:
R$^{1-4}$ are the same or different and are selected from the group consisting of H, D, alkyl, silyl, aryl, deuterated alkyl, deuterated silyl, deuterated aryl, and an electron-withdrawing group;
R$^5$ is selected from the group consisting of H, D, alkyl, aryl, deuterated alkyl and deuterated aryl; and
R$^6$-R$^9$ are the same or different and are selected from the group consisting of H, D, alkyl, silyl, aryl, deuterated alkyl, deuterated silyl, and deuterated aryl;
with the proviso that at least one of R$^{1-4}$ is an electron-withdrawing group.

There is also provided an organic electronic device comprising a first electrical contact, a second electrical contact and a photoactive layer therebetween, the photoactive layer comprising the compound having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
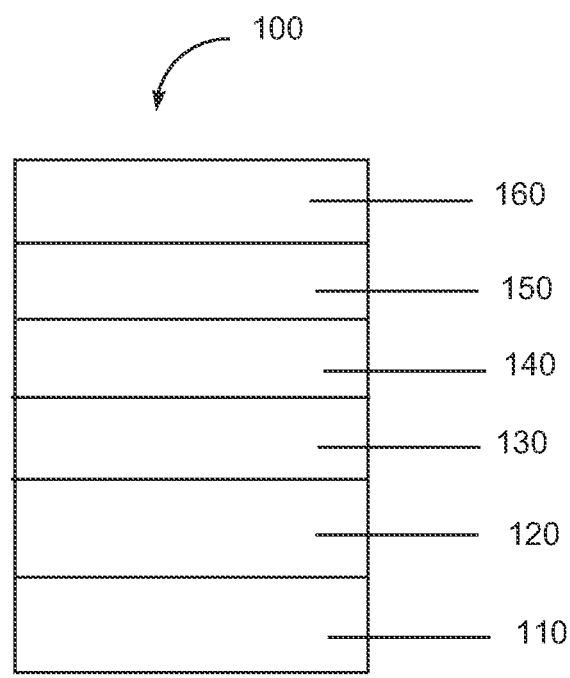
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound Having Formula I, Synthesis, Devices, and finally Examples.

1. DEFINITIONS AND CLARIFICATION OF TERMS

Before addressing details of embodiments described below, some terms are defined or clarified.

The term "alkoxy" is intended to mean a group having the formula —OR, which is attached via the oxygen, where R is an alkyl.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having delocalized pi electrons.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "arylene" is intended to mean a group derived from an aromatic hydrocarbon having two points of attachment. In some embodiments, an aryl group has from 3-60 carbon atoms.

The term "aryloxy" is intended to mean a group having the formula —OAr, which is attached via the oxygen, where Ar is an aryl.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen attached to carbon has been replaced by deuterium. The letter "D" is used to indicate deuterium. The term "deuterated analog" refers to a structural analog of a compound or group in which one or more available hydrogens attached to carbon have been replaced with deuterium. When "deuteration" is present, the material is deuterated. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electron-withdrawing" as it refers to a substituent group is intended to mean a group which would decrease the electron density of an aromatic ring. In some embodiments, the electron-withdrawing group ("EWG") is selected from the group consisting of fluoro, cyano, perfluoroalkyl, nitro, and —$SO_2R$, where R is alkyl or perfluoroalkyl.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm. The term "green luminescent material" is intended to mean a material capable of emitting radiation that has an emission maximum at a wavelength in a range of approximately 495-570 nm. The term "orange luminescent material" is intended to mean a material capable of emitting radiation that has an emission maximum at a wavelength in a range of approximately 590-620 nm. The term "red luminescent material" is intended to mean a material capable of emitting radiation that has an emission maximum at a wavelength in a range of approximately 620-750 nm. The term "yellow luminescent material" is intended to mean a material capable of emitting radiation that has an emission maximum at a wavelength in a range of approximately 570-590 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "secondary alkyl" refers to an alkyl group that is attached via a carbon which is bonded to two other carbons. Secondary alkyls include monocyclic alkyls.

The term "silyl" refers to the group $R_3Si$—, where R is H, D, C1-20 alkyl, deuterated alkyl, fluoroalkyl, aryl, or deuterated aryl. In some embodiments, one or more carbons in an R alkyl group are replaced with Si. In some embodiments, the alkyl, fluoroalkyl or aryl groups are deuterated.

The term "tertiary alkyl" refers to an alkyl group that is attached via a carbon which is bonded to three other carbons.

Unless otherwise indicated, all groups can be substituted or unsubstituted. In some embodiments, the substituents are selected from the group consisting of alkyl, alkoxy, aryl, and deuterated analogs thereof.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. COMPOUNDS HAVING FORMULA I

The new compounds described herein have Formula I

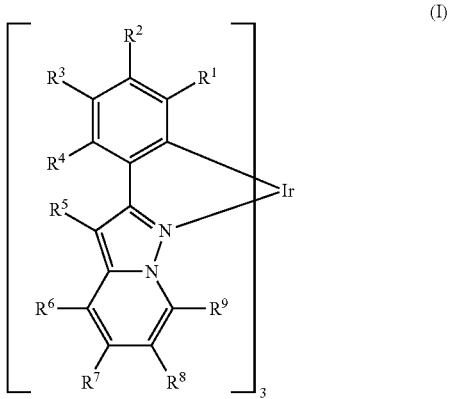

(I)

wherein:
$R^{1-4}$ are the same or different and are selected from the group consisting of H, D, alkyl, silyl, aryl, deuterated alkyl, deuterated silyl, deuterated aryl, and an electron-withdrawing group;
$R^5$ is selected from the group consisting of H, D, alkyl, aryl, deuterated alkyl and deuterated aryl; and
$R^6$-$R^9$ are the same or different and are selected from the group consisting of H, D, alkyl, silyl, aryl, deuterated alkyl, deuterated silyl, and deuterated aryl;
with the proviso that at least one of $R^{1-4}$ is an electron-withdrawing group.

In some embodiments, the compounds having Formula I are useful as emissive materials.

In some embodiments, the compounds having Formula I are blue emissive materials.

The compounds having Formula I can be used alone or as a dopant in a host material.

The compounds having Formula I are soluble in many commonly used organic solvents. Solutions of these compounds can be used for liquid deposition using techniques such as discussed above.

Unexpectedly, it has been found that the compounds having the substitution pattern shown in Formula I have improved efficiencies in devices. This is advantageous for reducing energy consumption in all types of devices, and particularly for lighting applications.

At least one of $R^{1-4}$ is an electron-withdrawing group. In some embodiments, the electron-withdrawing group ("EWG") is selected from the group consisting of fluoro, cyano, perfluoroalkyl, nitro, and —SO$_2$R, where R is alkyl or perfluoroalkyl. When more than one of $R^{1-4}$ is an EWG, the groups can be the same or different.

In some embodiments, $R^1$ is selected from the group consisting of H, D, alkyl having 1-10 carbons, deuterated alkyl having 1-10 carbons, aryl having 6-20 carbons, and deuterated aryl having 6-20 carbons.

In some embodiments, $R^1$ is selected from the group consisting of alkyl having 1-10 carbons and deuterated alkyl having 1-10 carbons.

In some embodiments, $R^1$ is selected from the group consisting of H and D.

In some embodiments, $R^1$ is an aryl or deuterated aryl having 6-20 carbons; in some embodiments, 6-12 carbons.

In some embodiments, $R^1$ is selected from the group consisting of phenyl, biphenyl, napthyl, and deuterated analogs thereof, wherein any of the previous groups may have one or more substituents that are alkyl groups with 1-10 carbons or deuterated alkyl groups with 1-10 carbons.

In some embodiments, $R^1$ is selected from the group consisting of phenyl, tolyl, xylyl, mesityl, and deuterated analogs thereof.

In some embodiments. $R^2$ is selected from the group consisting of H, D, alkyl having 1-10 carbons, deuterated alkyl having 1-10 carbons, aryl having 6-20 carbons, deuterated aryl having 6-20 carbons and an EWG.

In some embodiments, $R^2$ is an aryl or deuterated aryl having 6-20 carbons; in some embodiments, 6-12 carbons.

In some embodiments, $R^2$ is selected from the group consisting of phenyl, biphenyl, napthyl, and deuterated analogs thereof, wherein any of the previous groups may have one or more substituents that are alkyl groups with 1-10 carbons.

In some embodiments, $R^2$ is selected from the group consisting of phenyl, tolyl, xylyl, mesityl, and deuterated analogs thereof.

In some embodiments, $R^2$ is selected from the group consisting of H, D, F, and perfluoroalkyl.

In some embodiments, $R^3$ is selected from the group consisting of H, D, alkyl having 1-10 carbons, deuterated alkyl having 1-10 carbons, aryl having 6-20 carbons, and deuterated aryl having 6-20 carbons.

In some embodiments, $R^3$ is selected from the group consisting of H and D.

In some embodiments, $R^3$ is an aryl or deuterated aryl having 6-20 carbons; in some embodiments, 6-12 carbons.

In some embodiments, $R^3$ is selected from the group consisting of phenyl, biphenyl, napthyl, and deuterated analogs thereof, wherein any of the previous groups may have one or more substituents that are alkyl groups with 1-10 carbons.

In some embodiments, $R^3$ is selected from the group consisting of phenyl, tolyl, xylyl, mesityl, and deuterated analogs thereof.

In some embodiments, $R^4$ is selected from the group consisting of H, D, F, alkyl having 1-10 carbons, deuterated alkyl having 1-10 carbons, aryl having 6-20 carbons, deuterated aryl having 6-20 carbons, and an EWG.

In some embodiments, $R^4$ is an aryl or deuterated aryl having 6-20 carbons; in some embodiments, 6-12 carbons.

In some embodiments, $R^4$ is selected from the group consisting of phenyl, biphenyl, napthyl, and deuterated analogs thereof, wherein any of the previous groups may have one or more substituents that are alkyl groups with 1-10 carbons.

In some embodiments, $R^4$ is selected from the group consisting of phenyl, tolyl, xylyl, mesityl, and deuterated analogs thereof.

In some embodiments, $R^4$ is selected from the group consisting of H, D, F, and perfluoroalkyl.

In some embodiments. $R^5$ is selected from the group consisting of H, D, alkyl having 1-10 carbons, deuterated alkyl having 1-10 carbons, aryl having 6-20 carbons, and deuterated aryl having 6-20 carbons.

In some embodiments, $R^5$ is selected from the group consisting of alkyl having 1-10 carbons and deuterated alkyl having 1-10 carbons In some embodiments, $R^5$ is selected from the group consisting of H and D.

In some embodiments, $R^5$ is an aryl or deuterated aryl having 6-20 carbons; in some embodiments, 6-12 carbons.

In some embodiments, at least one of $R^6$-$R^9$ is an alkyl or deuterated alkyl having 1-20 carbons; in some embodiments, 1-10; in some embodiments, 3-8 carbons.

In some embodiments, at least one of $R^6$-$R^9$ is a secondary or tertiary alkyl group.

In some embodiments, at least one of $R^6$-$R^9$ is selected from the group consisting of 2-propyl, 2-butyl, 2-pentyl, cyclohexyl, methylcyclohexyl, and deuterated analogs thereof.

In some embodiments, one of $R^6$-$R^9$ is an alkyl or deuterated alkyl having 1-20 carbons, and the others of $R^6$-$R^9$ are H or D.

In some embodiments, one of $R^6$-$R^9$ is an alkyl or deuterated alkyl having 1-10 carbons.

In some embodiments, one of $R^8$ and $R^9$ is an aryl or deuterated aryl having 6-20 carbons; in some embodiments, 6-12 carbons.

In some embodiments, one of $R^8$ and $R^9$ is selected from the group consisting of phenyl, biphenyl, napthyl, and deuterated analogs thereof, wherein any of the previous groups may have one or more substituents that are alkyl groups or deuterated alkyl groups with 1-10 carbons.

In some embodiments, one of $R^3$ and $R^9$ is selected from the group consisting of phenyl, tolyl, xylyl, mesityl, and deuterated analogs thereof.

In some embodiments, $R^6$-$R^9$ are selected from H and D.

In some embodiments, $R^6$-$R^9$ are all D.

In some embodiments, two of $R^6$-$R^9$ are the same or different and are an alkyl or deuterated alkyl having 1-20 carbons, and two of $R^6$-$R^9$ are H or D. In some embodiments, the alkyl or deuterated alkyl has 1-10 carbons.

In some embodiments, three of $R^6$-$R^9$ are the same or different and are an alkyl or deuterated alkyl having 1-20 carbons, and one of $R^6$-$R^9$ is H or D. In some embodiments, the alkyl or deuterated alkyl has 1-10 carbons.

In some embodiments, at least one of $R^2$ and $R^4$ is an EWG. In some embodiments, both $R^2$ and $R^4$ are an EWG.

In some embodiments, $R^2$ and $R^4$ are the same.

In some embodiments, $R^2$ and $R^4$ are the same and are EWG.

In some embodiments, $R^2$ and $R^4$ are F or a perfluoroalkyl.

In some embodiments, $R^2$ and $R^4$ are F or $CF_3$.

In some embodiments, $R^2$ and $R^4$ are F or a perfluoroalkyl and at least one of $R^6$-$R^9$ is an alkyl or deuterated alkyl having 1-10 carbons.

In some embodiments, $R^2$ and $R^4$ are F or $CF_3$ and at least one of $R^6$-$R^9$ is an alkyl or deuterated alkyl having 1-10 carbons.

In some embodiments of the compound having Formula there can be any combination of the following:

(i) deuteration is present in one or more parts of the compound;

(ii) $R^1$ is H, D, alkyl having 1-10 carbons, deuterated alkyl having 1-10 carbons, aryl having 6-20 carbons, or deuterated aryl having 6-20 carbons;

(iii) $R^2$ is H, D, alkyl having 1-10 carbons, deuterated alkyl having 1-10 carbons, aryl having 6-20 carbons, deuterated aryl having 6-20 carbons, F, or perfluoroalkyl;

(iv) $R^3$ is H, D, alkyl having 1-10 carbons, or deuterated alkyl having 1-10 carbons;

(v) $R^4$ is H, D, alkyl having 1-10 carbons, deuterated alkyl having 1-10 carbons, aryl having 6-20 carbons, deuterated aryl having 6-20 carbons, F, or perfluoroalkyl;

(vi) $R^5$ is H or D;

(vii) $R^6$ is H, D, alkyl having 1-10 carbons, aryl having 6-20 carbons, deuterated alkyl having 1-10 carbons, or deuterated aryl having 6-20 carbons;

(viii) $R^7$ is H, D, alkyl having 1-10 carbons, aryl having 6-20 carbons, deuterated alkyl having 1-10 carbons, or deuterated aryl having 6-20 carbons;

(ix) $R^8$ is H, D, alkyl having 1-10 carbons, aryl having 6-20 carbons, deuterated alkyl having 1-10 carbons, or deuterated aryl having 6-20 carbons;

(x) $R^9$ is H, D, alkyl having 1-10 carbons, aryl having 6-20 carbons, deuterated alkyl having 1-10 carbons, or deuterated aryl having 6-20 carbons;

(xi) at least one of $R^6$-$R^9$ is an alkyl, aryl or deuterated analog thereof, or all $R^6$-$R^9$ are H or D; and (xii) $R^2$ and $R^4$ are F or perfluoroalkyl.

Any of the above embodiments can be combined with one or more of the other embodiments, so long as they are not mutually exclusive. For example, the embodiment in which $R^1$ is selected from the group consisting of alkyl having 1-10 carbons and deuterated alkyl having 1-10 carbons. can be combined with the embodiment in which $R^2$ is an aryl or deuterated aryl having 6-20 carbons; in some embodiments, 6-12 carbons. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula I include, but are not limited to, compounds B1 through B8 shown below.

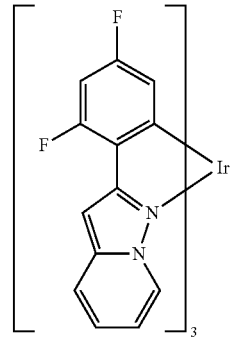

B1

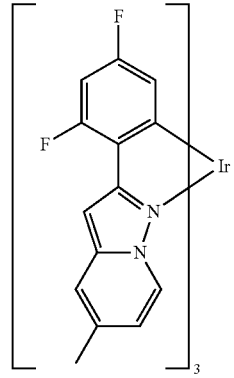

B2

-continued

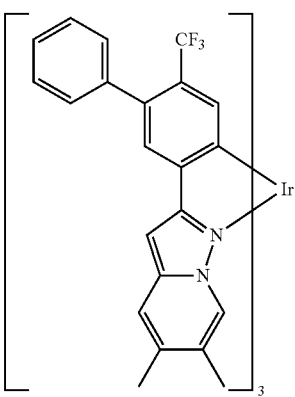
B3

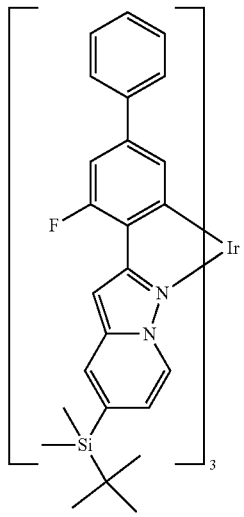
B6

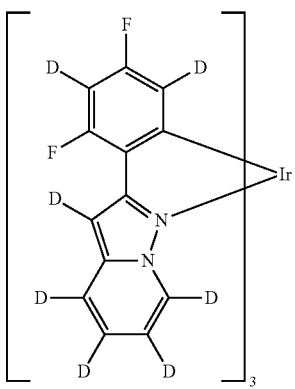
B4

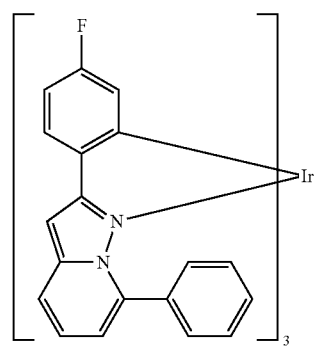
B7

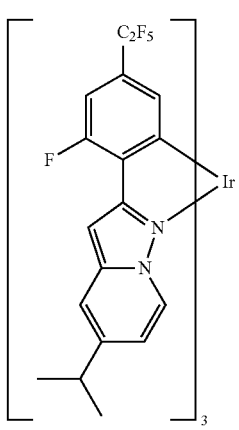
B5

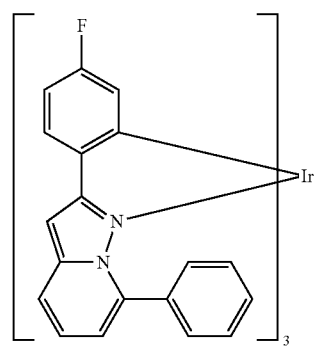
B8

3. SYNTHESIS

The phenyl-pyrazolopyridine ligands in the compound having Formula I can generally be prepared using known synthetic methods. In one exemplary method, a substituted or unsubstituted benzoylpyridinium ylide is reacted with a substituted or unsubstituted (E)-(2-iodovinyl)benzene.

The aforementioned ligands ("L") can be complexed to Ir(III) using known synthetic techniques, such as described in Grushin et al., U.S. Pat. No. 6,670,645, and Komo et al., Chem. Lett, 32, 252 (2003). One exemplary method uses a three-step synthesis. First, the "L₂IrCl dimer," is formed by reaction of indium(III) chloride hydrate with excess ligand L in a heated mixture of 2-ethoxyethanol and water. Next, the iridium triflate can be prepared by reaction of the L₂IrCl dimer with silver triflate. Finally, the iridium triflate can be reacted with excess ligand L in refluxing 2-ethoxyethanol to afford the cyclometallated $IrL_3$ compound as the fac-isomer.

Additional details are found in the examples.

4. DEVICES

Organic electronic devices that may benefit from having one or more layers comprising the compounds having Formula I described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

Figure 2:
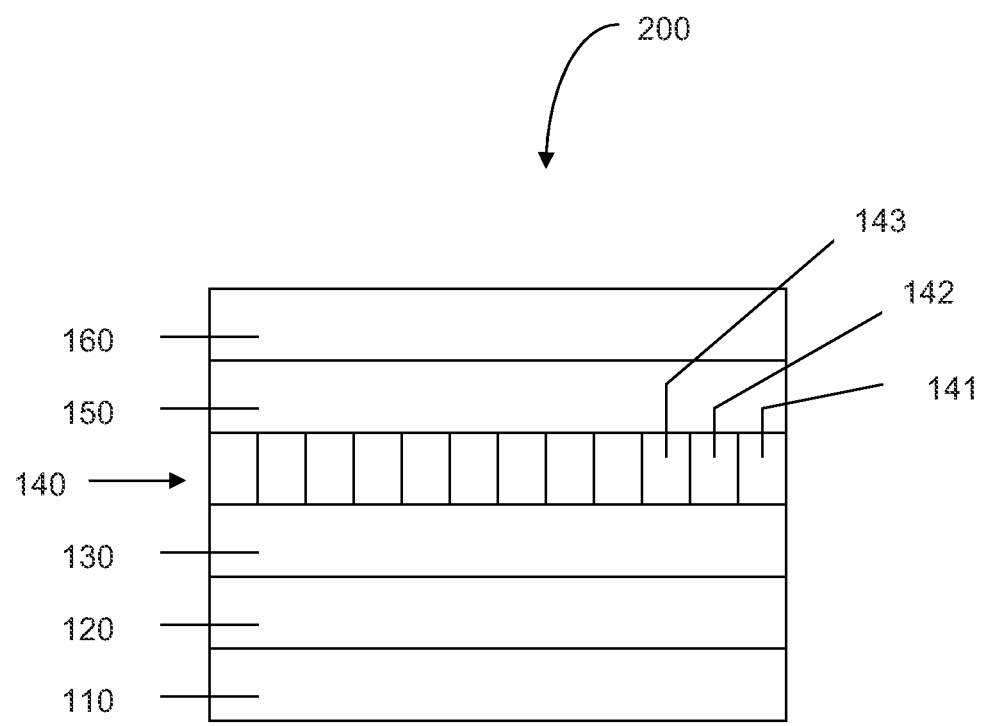
FIG. 2 includes another illustration of an organic light-emitting device.

In some embodiments, the photoactive layer is pixilated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, In some embodiments 1000-2000 Å; hole injection layer 120, 50-2000 Å, In some embodiments 200-1000 Å; hole transport layer 120, 50-2000 Å, In some embodiments 200-1000 Å; photoactive layer 130, 10-2000 Å, In some embodiments 100-1000 Å; layer 140, 50-2000 Å, In some embodiments 100-1000 Å; cathode 150, 200-10000 Å, in some embodiments 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I are useful as the emissive material in photoactive layer 140, having blue emission color. They can be used alone or as a dopant in one or more host materials.

Any of the compounds of Formula I represented by the embodiments, specific embodiments, and combination of embodiments discussed above can be used in the device.

a. Photoactive Layer

In some embodiments, the photoactive layer consists essentially of a compound having Formula I.

In some embodiments, the photoactive layer comprises a host material and a compound having Formula I as a dopant.

In some embodiments, the photoactive layer comprises a first host material, a second host material, and a compound having Formula I as a dopant.

In some embodiments, the photoactive layer consists essentially of a host material and a compound having Formula I as a dopant.

In some embodiments, the photoactive layer consists essentially of a first host material, a second host material, and a compound having Formula I as a dopant.

In some embodiments, when a host material is present, the weight ratio of dopant having Formula I to total host material is in the range of 1:99 to 40:60; in some embodiments 5:95 to 30:70; in some embodiments, 10:90 to 20:80.

In some embodiments, the host has a triplet energy level higher than that of the dopant, so that it does not quench the emission.

In some embodiments, the host is selected from the group consisting of carbazoles, indolocarbazoles, triazines, aryl ketones, phenylpyridines, pyrimidines, phenanthrolines, triarylamines, deuterated analogs thereof, combinations thereof, and mixtures thereof.

In some embodiments, the photoactive layer is intended to emit white light.

In some embodiments, the photoactive layer comprises a host, a compound of Formula I, and one or more additional dopants emitting different colors, so that the overall emission is white.

In some embodiments, the photoactive layer consists essentially of a host, a first dopant having Formula I, and a second dopant, where the second dopant emits a different color than the first dopant. In some embodiments, the emission color of the second dopant is yellow.

In some embodiments, the photoactive layer consists essentially of a host, a first dopant having Formula I, a second dopant, and a third dopant. In some embodiments, the emission color of the second dopant is red and the emission color of the third dopant is green.

Any kind of electroluminescent ("EL") material can be used as second and third dopants. EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the second and third dopants are cyclometallated complexes of Ir or Pt.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film.

In some embodiments, the liquid medium for the hole injection layer consists essentially of one or more organic solvents.

In some embodiments, the liquid medium for the hole injection layer consists essentially of water or water and an organic solvent.

The hole injection material can be present in the liquid medium in an amount from 0.5 to 10 percent by weight.

The hole injection layer can be applied by any continuous or discontinuous liquid deposition technique.

In some embodiments, the hole injection layer is applied by spin coating.

In some embodiments, the hole injection layer is applied by ink jet printing.

In some embodiments, the hole injection layer is applied by continuous nozzle printing.

In some embodiments, the hole injection layer is applied by slot-die coating.

After liquid deposition, the liquid medium can be removed in air, in an inert atmosphere, or by vacuum, at room temperature or with heating.

The hole transport layer can be deposited from any liquid medium in which it is dissolved or dispersed and from which it will form a film.

In some embodiments, the liquid medium for the hole transport layer consists essentially of one or more organic solvents.

In some embodiments, the liquid medium for the hole transport layer consists essentially of water or water and an organic solvent.

In some embodiments, the liquid medium for the hole transport layer includes an aromatic organic liquid.

In some embodiments, the liquid medium for the hole transport layer includes an organic liquid selected from the group consisting of chloroform, dichloromethane, chlorobenzene, dichlorobenzene, toluene, xylene, mesitylene, anisole, aromatic ethers, aromatic esters, and mixtures thereof.

The hole transport material can be present in the liquid medium in a concentration of 0.2 to 2 percent by weight.

The hole transport layer can be applied by any continuous or discontinuous liquid deposition technique.

In some embodiments, the hole transport layer is applied by spin coating.

In some embodiments, the hole transport layer is applied by ink jet printing.

In some embodiments, the hole transport layer is applied by continuous nozzle printing.

In some embodiments, the hole transport layer is applied by slot-die coating.

After liquid deposition, the liquid medium can be removed in air, in an inert atmosphere, or by vacuum, at room temperature or with heating.

The photoactive layer can be deposited from any liquid medium in which it is dissolved or dispersed and from which it will form a film.

In some embodiments, the liquid medium for the photoactive layer consists essentially of one or more organic solvents.

In some embodiments, the liquid medium for the photoactive layer consists essentially of water or water and an organic solvent.

In some embodiments, the liquid medium for the photoactive layer includes an aromatic solvent.

In some embodiments, the liquid medium for the photoactive layer is selected from the group consisting of chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, aromatic ethers, aromatic esters, and mixtures thereof.

In some embodiments, the photoactive material is present in the liquid medium in a concentration of 0.2 to 2 percent by weight. Other weight percentages of photoactive material may be used depending upon the liquid medium.

The photoactive layer can be applied by any continuous or discontinuous liquid deposition technique.

In some embodiments, the photoactive layer is applied by spin coating.

In some embodiments, the photoactive layer is applied by ink jet printing.

In some embodiments, the photoactive layer is applied by continuous nozzle printing.

In some embodiments, the photoactive layer is applied by slot-die coating.

After liquid deposition, the liquid medium can be removed in air, in an inert atmosphere, or by vacuum, at room temperature or with heating.

In some embodiments, the electron transport layer is deposited by vapor deposition. The electron transport layer can be deposited by any vapor deposition method. In some embodiments, it is deposited by thermal evaporation under vacuum.

In some embodiments, the electron transport layer is deposited by vapor deposition. The electron injection layer can be deposited by any vapor deposition method. In some embodiments, it is deposited by thermal evaporation under vacuum.

In some embodiments, the cathode is formed by vapor deposition. The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Example 1

This example illustrates the preparation of compound B1.

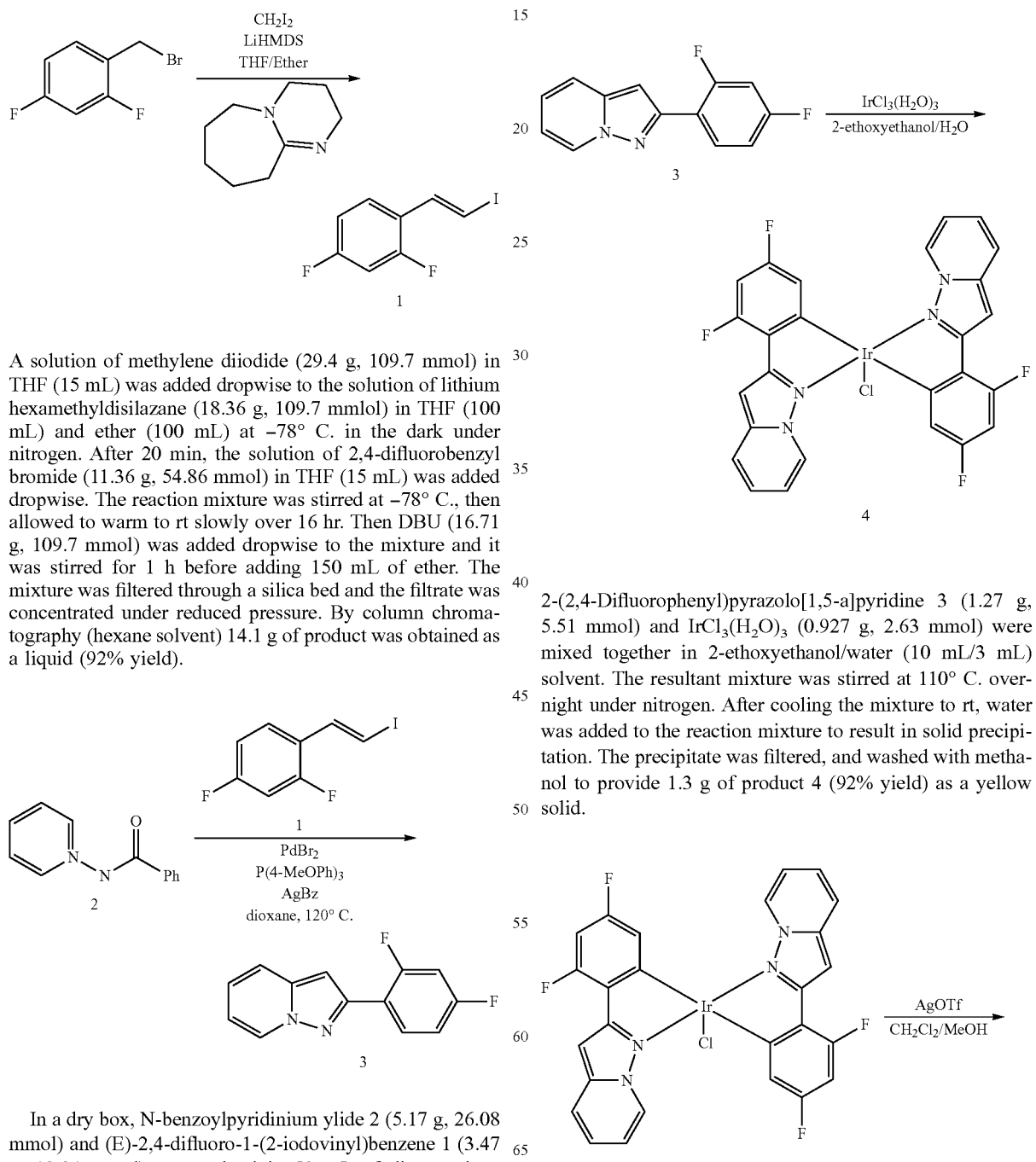

A solution of methylene diiodide (29.4 g, 109.7 mmol) in THF (15 mL) was added dropwise to the solution of lithium hexamethyldisilazane (18.36 g, 109.7 mmlol) in THF (100 mL) and ether (100 mL) at −78° C. in the dark under nitrogen. After 20 min, the solution of 2,4-difluorobenzyl bromide (11.36 g, 54.86 mmol) in THF (15 mL) was added dropwise. The reaction mixture was stirred at −78° C., then allowed to warm to rt slowly over 16 hr. Then DBU (16.71 g, 109.7 mmol) was added dropwise to the mixture and it was stirred for 1 h before adding 150 mL of ether. The mixture was filtered through a silica bed and the filtrate was concentrated under reduced pressure. By column chromatography (hexane solvent) 14.1 g of product was obtained as a liquid (92% yield).

In a dry box, N-benzoylpyridinium ylide 2 (5.17 g, 26.08 mmol) and (E)-2,4-difluoro-1-(2-iodovinyl)benzene 1 (3.47 g, 13.04 mmol) were mixed in 50 mL of dioxane in a pressure bottle. Then the solution of tris(4-methoxyphenyl) phosphine (0.69 g, 1.96 mmol) and PdBr$_2$ (0.173 g, 0.652 mmol) in 10 mL of dioxane was added to the mixture, followed by the silver benzoate (8.95 g, 39.12 mmol). Outside dry box the mixture was stirred at 120° C. for 16 h. After cooling the mixture to rt, methylene chloride was added to the mixture, then the resultant mixture was filtered through silica bed. Saturated NaHCO$_3$ solution was added to the filtrate, and the separated organic layer was dried over anhydrous MgSO$_4$. By column chromatography (5-10% ethyl acetate in hexane) 2 g of product 3 was obtained as a solid (66% yield).

2-(2,4-Difluorophenyl)pyrazolo[1,5-a]pyridine 3 (1.27 g, 5.51 mmol) and IrCl$_3$(H$_2$O)$_3$ (0.927 g, 2.63 mmol) were mixed together in 2-ethoxyethanol/water (10 mL/3 mL) solvent. The resultant mixture was stirred at 110° C. overnight under nitrogen. After cooling the mixture to rt, water was added to the reaction mixture to result in solid precipitation. The precipitate was filtered, and washed with methanol to provide 1.3 g of product 4 (92% yield) as a yellow solid.

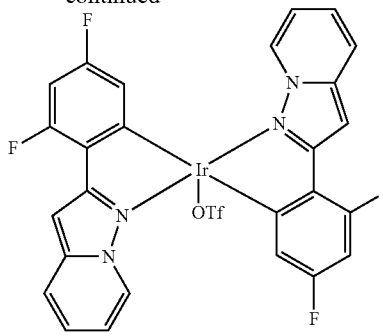

5

The reaction mixture of iridium chloride 4 (1.3 g, 0.947 mmol) and silver Inflate (0.486 g, 1.89 mmol) in CH$_2$Cl$_2$/MeOH (24 mL/1.3 mL) was refluxed for 24 h. After cooling the mixture to rt, it was filtered through a column. The filtrate was concentrated under reduced pressure to provide a greenish solid (1.35 g) as a product 5 (89% yield).

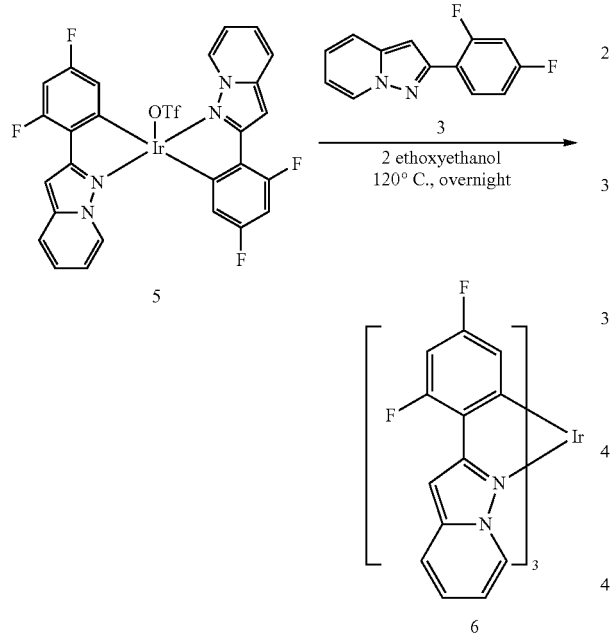

The mixture of iridium triflate 5 (1.2 g, 1.5 mmol) and 2-(2,4-difluorophenyl)pyrazolo[1,5-a]pyridine 3 (0.69 g, 3.0 mmol) in 2-ethoxyethanol (25 mL) was stirred at 120° C. under nitrogen for 3 days. After cooling the mixture to rt, water was added to the mixture. The precipitated solid was filtered and purified by column chromatography (methylene chloride as an eluent) to provide 0.3 g of desired product 6 (23% yield) as a fac-isomer.

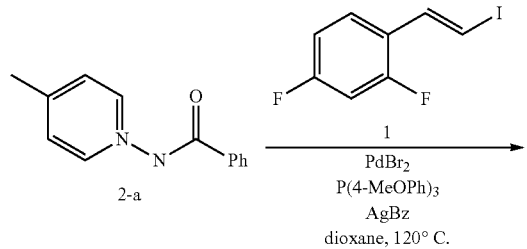

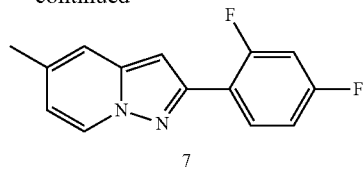

7

In a dry box, N-benzoylpyridinium ylide 2-a (2.7 g, 12.54 mmol) and (E)-2,4-difluoro-1-(2-iodovinyl)benzene 1 (1.66 g, 6.27 mmol) were mixed in 40 mL of dioxane in a pressure bottle. Then the solution of tris(4-methoxyphenyl)phosphine (0.33 g, 0.94 mmol) and PdBr$_2$ (0.083 g, 0.313 mmol) in 5 mL of dioxane was added to the mixture, followed by the silver benzoate (4.31 g, 18.81 mmol). Outside dry box the mixture was stirred at 120° C. for 16 h. After cooling the mixture to rt, methylene chloride was added to the mixture, then the resultant mixture was filtered through silica bed. Saturated NaHCO$_3$ solution was added to the filtrate, and the separated organic layer was dried over anhydrous MgSO$_4$. By column chromatography (2-3% ethyl acetate in hexane) 0.8 g of product 7 was obtained as a solid (52% yield).

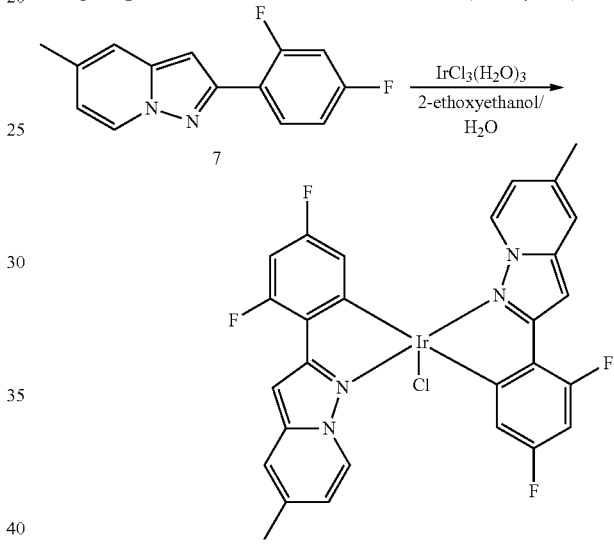

2-(2,4-Difluorophenyl)-5-methylpyrazolo[1,5-a]pyridine 7 (0.6 g, 2.45 mmol) and IrCl$_3$(H$_2$O)$_3$ (0.433 g, 1.22 mmol) were mixed together in 2-ethoxyethanol/water (8 mL/2 mL) solvent. The resultant mixture was stirred at 110° C. for 2 days under nitrogen. After cooling the mixture to rt, water was added to the reaction mixture to result in solid precipitation. The precipitate was filtered, and washed with water and methanol to provide 0.68 g of yellow filter cake as a product 8 (78% yield).

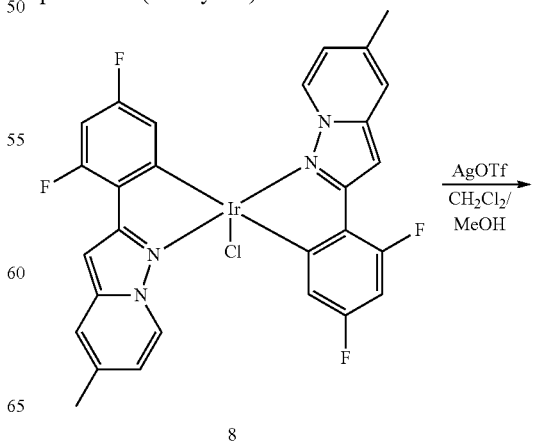

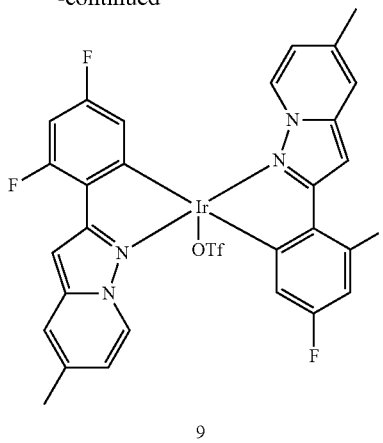

9

The reaction mixture of iridium chloride 8 (0.68 g, 0.95 mmol) and silver triflate (0.244 g, 0.95 mmol) in CH$_2$Cl$_2$/MeOH (12 mL/1.5 mL) was refluxed for 18 h. After cooling the mixture to rt, it was filtered through a column. The filtrate was concentrated under reduced pressure to provide a greenish solid (0.78 g) as a product 9 (99% yield).

modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

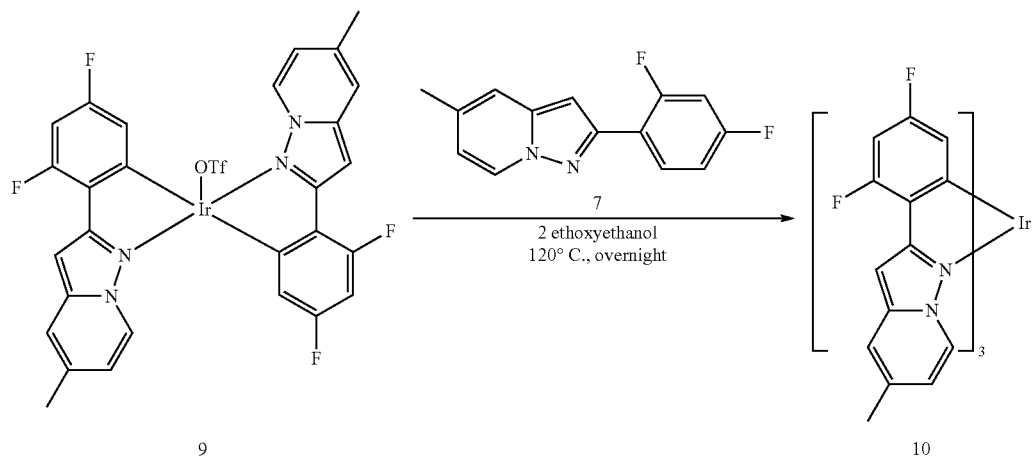

The mixture of iridium triflate 9 (0.75 g, 0.91 mmol) and 2-(2,4-difluorophenyl)-5-methylpyrazolo[1,5-a]pyridine 7 (0.44 g, 1.82 mmol) in 2-ethoxyethanol (20 mL) was stirred at 120° C. under nitrogen for 20 h. After cooling the mixture to rt, water was added to the mixture. The precipitated solid was filtered and purified by column chromatography (10-35% methylene chloride in hexane) to provide 0.1 g of desired product 10 (13% yield) as a fac-isomer.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various

What is claimed is:
1. A compound having Formula I

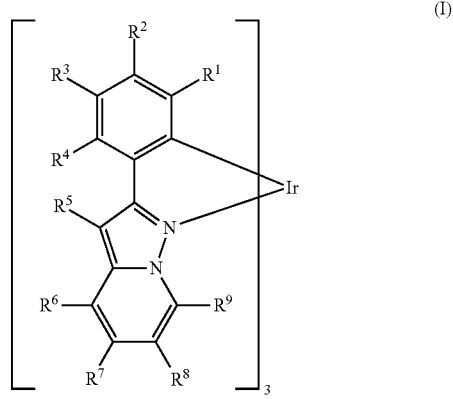

(I)

wherein:
   $R^{1-4}$ are the same or different and are selected from the group consisting of H, D, alkyl, silyl, aryl, deuterated alkyl, deuterated silyl, deuterated aryl, and an electron-withdrawing group;
   $R^5$ is selected from the group consisting of H, D, alkyl, aryl, deuterated alkyl and deuterated aryl; and
   $R^6$-$R^9$ are the same or different and are selected from the group consisting of H, D, alkyl, silyl, aryl, deuterated alkyl, deuterated silyl, and deuterated aryl; with the proviso that at least one of $R^{1-4}$ is an electron-withdrawing group, and with the proviso that at least one of $R^2$ or $R^4$ is selected from the group consisting of alkyl having 1-10 carbons, aryl having 6-20 carbons, an electron-withdrawing group, and deuterated analogs thereof, or $R^1$, $R^3$, $R^5$, or $R^9$ is selected from the group consisting of alkyl having 1-10 carbons, aryl having 6-20 carbons, and deuterated analogs thereof, or at least one of $R^6$ or $R^7$ is selected from the group consisting of alkyl having 1-10 carbons and deuterated analogs thereof.

2. The compound of claim 1, wherein $R^1$ is selected from the group consisting of alkyl having 1-10 carbons, aryl having 6-20 carbons, and deuterated analogs thereof.

3. The compound of claim 1, wherein $R^2$ is selected from the group consisting of alkyl having 1-10 carbons, aryl having 6-20 carbons, an electron-withdrawing group, and deuterated analogs thereof.

4. The compound of claim 1, wherein $R^3$ is selected from the group consisting of alkyl having 1-10 carbons, aryl having 6-20 carbons, and deuterated analogs thereof.

5. The compound of claim 1, wherein $R^4$ is selected from the group consisting of alkyl having 1-10 carbons, aryl having 6-20 carbons, an electron-withdrawing group, and deuterated analogs thereof.

6. The compound of claim 1, wherein at least one of $R^6$-$R^9$ is an alkyl or deuterated alkyl having 1-20 carbons.

7. The compound of claim 1, wherein one of $R^8$ and $R^9$ is an aryl or deuterated aryl having 6-20 carbons.

8. The compound of claim 1, wherein $R^6$-$R^9$ are selected from the group consisting of H and D.

9. The compound of claim 1, wherein $R^2$ or $R^4$ is an electron-withdrawing group.

10. The compound of claim 9, wherein the electron-withdrawing group is F or a perfluoroalkyl.

11. The compound of claim 9, wherein at least one of $R^6$-$R^9$ is an alkyl or deuterated alkyl having 1-10 carbons.

12. A compound selected from the group consisting of Compound B2, Compound B3, Compound B5, Compound B6, Compound B7 and Compound B8:

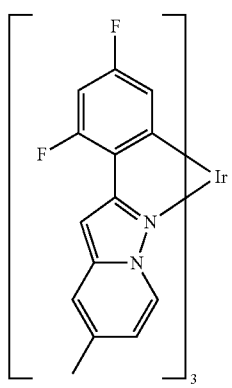

B2

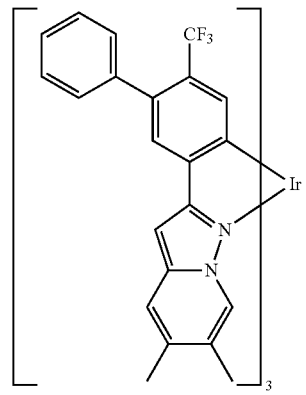

B3

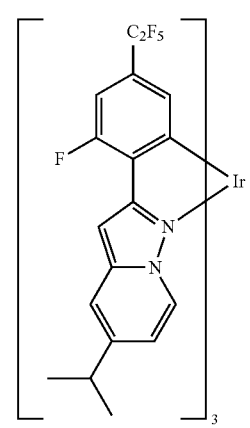

B5

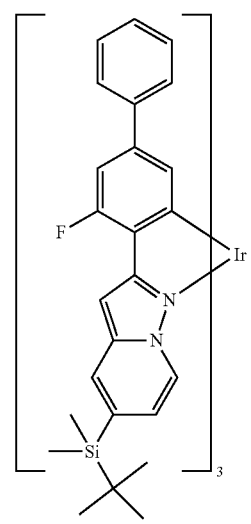

B6

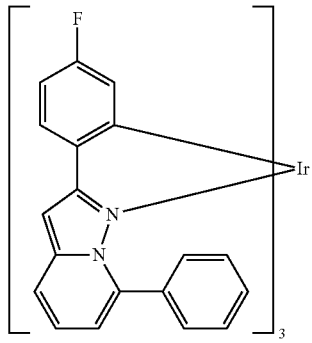

B7

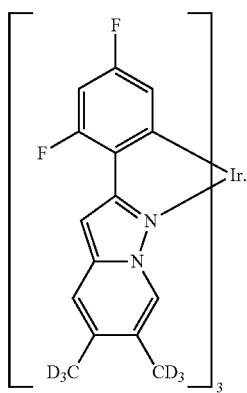

B8

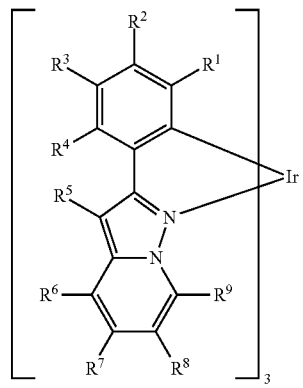

(I)

13. An organic electronic device comprising a first electrical contact, a second electrical contact and a photoactive layer therebetween, the photoactive layer comprising a compound having Formula I $R^{1-4}$ are the same or different and are selected from the group consisting of H, D, alkyl, silyl, aryl, deuterated alkyl, deuterated silyl, deuterated aryl, and an electron-withdrawing group;

$R^5$ is selected from the group consisting of H, D, alkyl, aryl, deuterated alkyl and deuterated aryl; and $R^6$-$R^9$ are the same or different and are selected from the group consisting of H, D, alkyl, silyl, aryl, deuterated alkyl, deuterated silyl, and deuterated aryl; with the proviso that at least one of $R^{1-4}$ is an electron-withdrawing group, and with the proviso that at least one of $R^2$ or $R^4$ is selected from the group consisting of alkyl having 1-10 carbons, aryl having 6-20 carbons, an electron-withdrawing group, and deuterated analogs thereof, or $R^1$, $R^3$, $R^8$, or $R^9$ is selected from the group consisting of alkyl having 1-10 carbons, aryl having 6-20 carbons, and deuterated analogs thereof, or at least one of $R^6$ or $R^7$ is selected from the group consisting of alkyl having 1-10 carbons and deuterated analogs thereof.

14. The organic electronic device of claim 13, wherein the photoactive layer comprises the compound of Formula I and further comprises a host material.

15. The organic electronic device of claim 14, wherein the photoactive layer consists essentially of the compound of Formula I and a host material.

* * * * *